US010543290B2

(12) United States Patent
Shur et al.

(10) Patent No.: US 10,543,290 B2
(45) Date of Patent: Jan. 28, 2020

(54) ULTRAVIOLET ILLUMINATOR FOR OBJECT DISINFECTION

(71) Applicant: Sensor Electronic Technology, Inc., Columbia, SC (US)

(72) Inventors: Michael Shur, Vienna, VA (US); Alexander Dobrinsky, Silver Spring, MD (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 15/857,822

(22) Filed: Dec. 29, 2017

(65) Prior Publication Data

US 2018/0185529 A1    Jul. 5, 2018

Related U.S. Application Data

(60) Provisional application No. 62/440,000, filed on Dec. 29, 2016.

(51) Int. Cl.
| | |
|---|---|
| *A61L 2/10* | (2006.01) |
| *A61L 2/08* | (2006.01) |
| *G01V 9/00* | (2006.01) |
| *G01N 21/64* | (2006.01) |

(52) U.S. Cl.
CPC ............... *A61L 2/10* (2013.01); *A61L 2/084* (2013.01); *G01V 9/00* (2013.01); *A61L 2202/14* (2013.01); *G01N 21/6486* (2013.01)

(58) Field of Classification Search
CPC ..................................... A61L 2/00; A61L 2/10
USPC ........................................ 250/454.11, 455.11
See application file for complete search history.

(56) References Cited

U.S. PATENT DOCUMENTS

| | | | |
|---|---|---|---|
| 7,553,456 B2 | 6/2009 | Gaska et al. |
| 7,634,996 B2 | 12/2009 | Gaska et al. |
| 8,277,734 B2 | 10/2012 | Koudymov et al. |
| 8,980,178 B2 | 3/2015 | Gaska et al. |
| 9,006,680 B2 | 4/2015 | Bettles et al. |
| 9,034,271 B2 | 5/2015 | Shur et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,707,307 B2 | 7/2017 | Shur et al. |
| 9,718,706 B2 | 8/2017 | Smetona et al. |

(Continued)

*Primary Examiner* — Jason L McCormack
(74) *Attorney, Agent, or Firm* — LaBatt, LLC

(57) ABSTRACT

Aspects of the invention provide a disinfecting pad for disinfecting and sterilizing objects. A plurality of pixelated light emitting sources are located on the flexible pad in an array, wherein a pixel characteristic radius is approximately $\frac{1}{10}$ millimeter to approximately 1 centimeter and the plurality of pixelated light emitting sources covers at least 25% of the flexible pad. Each of the plurality of pixelated light emitting sources includes at least one ultraviolet radiation source. The system includes set of sensors for acquiring data for the at least one object, wherein the data includes a presence and a location of the at least one object. A control system for selectively operating the at least one ultraviolet radiation source of the plurality of pixelated light emitting sources based on the presence and the location of the at least one object.

20 Claims, 9 Drawing Sheets

(56) References Cited

U.S. PATENT DOCUMENTS

| | | |
|---|---|---|
| 9,724,441 B2 | 8/2017 | Shur et al. |
| 9,750,830 B2 | 9/2017 | Shur et al. |
| 9,757,486 B2 | 9/2017 | Dobrinsky et al. |
| 9,795,699 B2 | 10/2017 | Shur et al. |
| 9,801,965 B2 | 10/2017 | Bettles et al. |
| 9,802,840 B2 | 10/2017 | Shturm et al. |
| 10,099,944 B2 | 10/2018 | Smetona et al. |
| 2013/0048545 A1 | 2/2013 | Shatalov et al. |
| 2014/0060104 A1 | 3/2014 | Shur et al. |
| 2014/0202962 A1 | 7/2014 | Bilenko et al. |
| 2014/0305470 A1* | 10/2014 | Desu-Kalyanam ......... A47L 23/263 134/6 |
| 2015/0165079 A1 | 6/2015 | Shur et al. |
| 2015/0265734 A1* | 9/2015 | Horioka ............ A61N 5/0624 250/492.1 |
| 2015/0297767 A1 | 10/2015 | Gaska et al. |
| 2015/0336810 A1 | 11/2015 | Smetona et al. |
| 2016/0000953 A1 | 1/2016 | Bettles et al. |
| 2016/0114186 A1 | 4/2016 | Dobrinsky et al. |
| 2016/0128526 A1* | 5/2016 | Dobrinsky ............ E03D 9/08 4/233 |
| 2016/0324996 A1 | 11/2016 | Bilenko et al. |
| 2016/0354502 A1* | 12/2016 | Simmons ............... A61L 2/10 |
| 2017/0057842 A1 | 3/2017 | Dobrinsky et al. |
| 2017/0100494 A1 | 4/2017 | Dobrinsky et al. |
| 2017/0100495 A1 | 4/2017 | Shur et al. |
| 2017/0100496 A1 | 4/2017 | Shur et al. |
| 2017/0189711 A1 | 7/2017 | Shur et al. |
| 2017/0245527 A1 | 8/2017 | Dobrinsky et al. |
| 2017/0245616 A1 | 8/2017 | Lakios et al. |
| 2017/0281812 A1 | 10/2017 | Dobrinsky et al. |
| 2017/0290934 A1 | 10/2017 | Dobrinsky et al. |
| 2017/0368215 A1 | 12/2017 | Shatalov et al. |
| 2018/0028700 A1 | 2/2018 | Dobrinsky et al. |
| 2018/0092308 A1 | 4/2018 | Barber, III et al. |
| 2018/0104368 A1 | 4/2018 | Dobrinsky et al. |
| 2018/0117194 A1 | 5/2018 | Dobrinsky et al. |

\* cited by examiner

ULTRAVIOLET ILLUMINATOR FOR OBJECT DISINFECTION

REFERENCE TO RELATED APPLICATIONS

The current application claims the benefit of U.S. Provisional Application No. 62/440,000, filed on 29 Dec. 2016, which is hereby incorporated by reference.

TECHNICAL FIELD

The disclosure relates generally to disinfection and sterilization, and more particularly, to the disinfection and sterilization of objects located on a flexible pad.

BACKGROUND ART

Ultraviolet water, air, and surface sterilization systems are known and have a successful history of development. The main unit of these ultraviolet systems is a source of ultraviolet radiation having wavelength(s) close to the absorption peaks of biologically significant molecules of DNA and proteins. The system can sterilize a medium to a safe condition as long as the power of the ultraviolet source and an exposure time are sufficient to destroy the internal biomolecular structure of the bacteria, viruses, protozoa and germs.

Known ultraviolet sterilization systems use mercury lamps or deep UV light emitting diodes as a source of ultraviolet radiation. Low-pressure and medium-pressure mercury lamps provide a linear spectrum of radiation with some lines, which wavelengths are in the relative vicinity to a DNA absorption line. A low-pressure mercury lamp with a main peak at 253.4 nm is often used in low-consumption residential water and air purification systems. Medium-pressure mercury lamps with a higher radiation power have a multi-peak radiation spectrum and are often used in municipal systems with medium and high water consumption.

However, the use of mercury lamps has significant drawbacks. For example, mercury lamps are fragile and bulky. Also, mercury is an extremely dangerous element, which implies serious limitations on applications of the mercury-based water purification systems. In particular, mercury lamps are not practical for use in transport and individual systems. Furthermore, a typical operating lifetime of a mercury lamp is less than 10,000 hours. An additional limitation is an inability to adjust or control a radiation spectrum of the mercury lamp. To this extent, the peaks of a mercury lamp do not exactly coincide with the absorption peaks of DNA and proteins, thereby decreasing the sterilization efficiency.

Some approaches have sought to minimize one or more drawbacks of mercury lamp-based sterilization. For example, one approach proposes a handheld ultraviolet water purification system based on a miniature mercury lamp. The design is targeted to overcome the size and portability drawbacks of traditional mercury lamp-based ultraviolet purifying systems. Nevertheless, the need for contact and even steering the sterilizing water with a fragile quartz sleeve with the mercury lamp inside makes the device dangerous for residential applications and not appropriate for transport, field, and portable applications.

SUMMARY OF THE INVENTION

Aspects of the invention provide a disinfecting pad for disinfecting and sterilizing objects. In an embodiment, a system includes a flexible pad for disinfecting the at least one object. A plurality of pixelated light emitting sources are located on the flexible pad in an array, wherein a pixel characteristic radius is approximately $\frac{1}{10}$ millimeter to approximately 1 centimeter and the plurality of pixelated light emitting sources covers at least 25% of the flexible pad. Each of the plurality of pixelated light emitting sources includes at least one ultraviolet radiation source. The system includes set of sensors for acquiring data for the at least one object, wherein the data includes a presence and a location of the at least one object. A control system for selectively operating the at least one ultraviolet radiation source of the plurality of pixelated light emitting sources based on the presence and the location of the at least one object.

A first aspect of the invention provides a system, comprising: a flexible pad for disinfecting at least one object; a plurality of pixelated light emitting sources located on the flexible pad in an array, wherein a pixel characteristic radius is approximately $\frac{1}{10}$ millimeter to approximately 1 centimeter and the plurality of pixelated light emitting sources covers at least 25% of the flexible pad, and wherein each of the plurality of pixelated light emitting sources includes at least one ultraviolet radiation source; a set of sensors for acquiring data for the at least one object, wherein the data includes a presence and a location of the at least one object; and a control system for selectively operating the at least one ultraviolet radiation source of the plurality of pixelated light emitting sources based on the presence and the location of the at least one object.

A second aspect of the invention provides a system, comprising: at least one object; a flexible pad for disinfecting the at least one object; a plurality of pixelated light emitting sources located on the flexible pad in an array, wherein a pixel characteristic radius is approximately $\frac{1}{10}$ millimeter to approximately 1 centimeter and the plurality of pixelated light emitting sources covers at least 25% of the flexible pad, and wherein each of the plurality of pixelated light emitting sources includes: at least one ultraviolet radiation source configured to generate ultraviolet radiation; and a set of sensors for acquiring data for the at least one object, wherein the data includes a presence and a location of the at least one object; and a control system for selectively operating the at least one ultraviolet radiation source of the plurality of pixelated light emitting sources based on the presence and the location of the at least one object.

A third aspect of the invention provides a system, comprising: at least one object; a flexible pad for disinfecting the at least one object; a plurality of pixelated light emitting sources located on the flexible pad in an array, wherein a pixel characteristic radius is approximately $\frac{1}{10}$ millimeter to approximately 1 centimeter and the plurality of pixelated light emitting sources covers at least 25% of the flexible pad, and wherein each of the plurality of pixelated light emitting sources includes: at least one ultraviolet radiation source configured to generate ultraviolet radiation; a set of visible light sources; and a set of sensors for acquiring data for the at least one object, wherein the data includes a presence and a location of the at least one object; and a control system for selectively operating the at least one ultraviolet radiation source of the plurality of pixelated light emitting sources based on the presence and the location of the at least one object.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
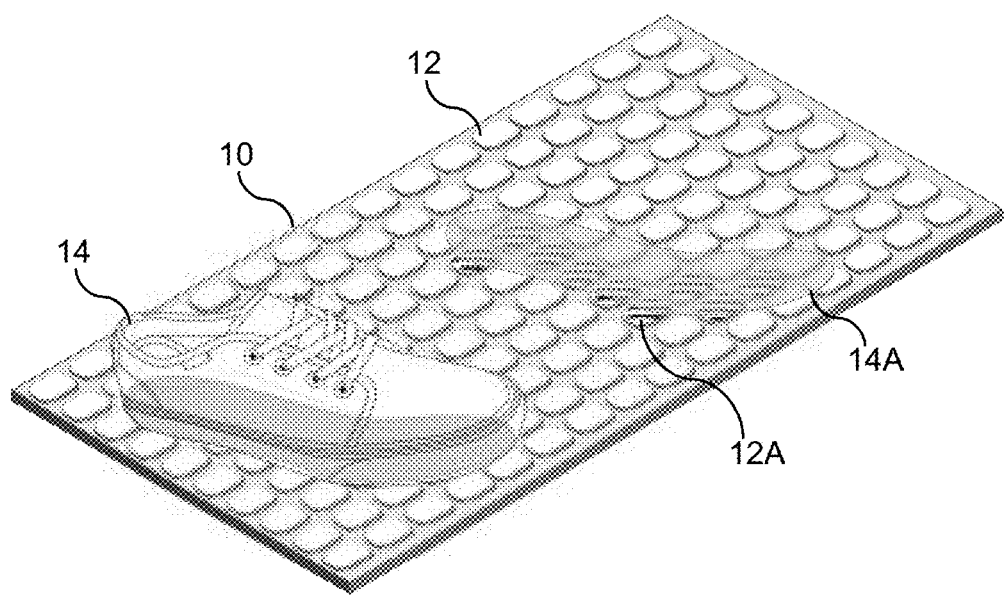
FIG. 1 shows a schematic view of an illustrative disinfecting pad according to an embodiment.

As indicated above, aspects of the invention provide a disinfecting pad for disinfecting and sterilizing objects. In an embodiment, a system includes a flexible pad for disinfecting the at least one object. A plurality of pixelated light emitting sources are located on the flexible pad in an array, wherein a pixel characteristic radius is approximately 1/10 millimeter to approximately 1 centimeter and the plurality of pixelated light emitting sources covers at least 25% of the flexible pad. Each of the plurality of pixelated light emitting sources includes at least one ultraviolet radiation source. The system includes set of sensors for acquiring data for the at least one object, wherein the data includes a presence and a location of the at least one object. A control system for selectively operating the at least one ultraviolet radiation source of the plurality of pixelated light emitting sources based on the presence and the location of the at least one object.

As used herein, a cleaning treatment of an object can entail sanitizing, disinfecting, and/or sterilizing the object. Sanitizing generally means reducing the number of bacterial contaminants to a predetermined safe level. Disinfecting generally means destroying pathogenic and other types of microorganisms, while sterilizing can be more extensive in that it kills all microbial forms and/or include destroying the ability of the microbial forms to reproduce.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

Generally, ultraviolet radiation, and in particular, UV-B radiation and UV-C radiation, is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 to about 280 nm provides the highest germicidal effectiveness, while an ultraviolet radiation between about 260 nm to about 310 nm is sufficient for providing overall germicidal effectiveness. While susceptibility to ultraviolet radiation varies, exposure to ultraviolet energy in the above range for about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through.

Also, as used herein, unless otherwise noted, the term "set" means one or more (i.e., at least one) and the phrase "any solution" means any now known or later developed solution. The singular forms "a," "an," and "the" include the plural forms as well, unless the context clearly indicates otherwise. Additionally, the terms "comprises," "includes," "has," and related forms of each, when used in this specification, specify the presence of stated features, but do not preclude the presence or addition of one or more other features and/or groups thereof.

It is understood that, unless otherwise specified, each value is approximate and each range of values included herein is inclusive of the end values defining the range. As used herein, unless otherwise noted, the term "approximately" is inclusive of values within +/−ten percent of the stated value, while the term "substantially" is inclusive of values within +/−five percent of the stated value. Unless otherwise stated, two values are "similar" when the smaller value is within +/−twenty-five percent of the larger value. As used herein, a "characteristic size" of an object corresponds to a measurement of the physical size of the object that defines its influence on a system.

Figure 2A:
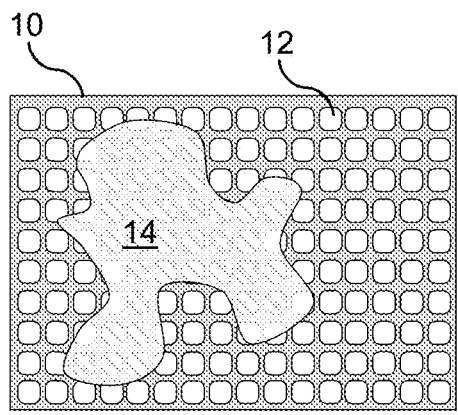
FIGS. 2A and 2B show a top view and a perspective view, respectively, of illustrative disinfecting pads according to embodiments.
Figure 2B:
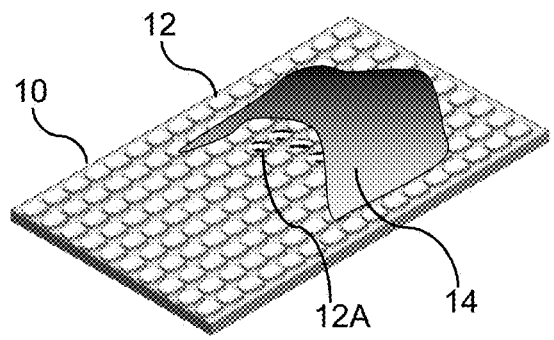

Turning to the drawings, FIG. 1 shows a schematic view of an illustrative disinfecting pad 10 including a plurality of pixelated light emitting sources 12, wherein pixelated refers to an array of relatively small sources. In an embodiment, the size of each light emitting source 12 is approximately 10% or less of the characteristic size of the disinfecting pad 10. The disinfecting pad 10 can be formed of any flexible material, such as a flexible fabric, a flexible plastic, a rubber material, and/or the like. In an embodiment, the disinfecting pad 10 can be formed of a material that is reflective of ultraviolet radiation. In a more specific embodiment, the disinfecting pad 10 can include a surface that is diffusively reflective. The plurality of light emitting sources 12 can form an array of ultraviolet radiation sources for an illuminating system. The array forms a set of pixels spaced sufficiently close and sufficiently small to resolve an object 14 located over the disinfecting pad 10. It is understood that the disinfecting pad 10 can be used to disinfect and sterilize any object. For example, as shown in FIG. 1, the disinfecting pad 10 can be used to disinfect a shoe 14. However, as shown in FIG. 2A, an object 14 can include any shape and/or size. Also, as shown in FIG. 2B, the shape of the object 14 does not need to lay flat across the top of the disinfecting pad 10 and the plurality of light emitting sources 12. In this embodiment, only the object 14 only touches the disinfecting pad 10 in several locations, but the plurality of light emitting sources 12A located beneath the object 14 are activated even though the object 14 does not touch all of the plurality of light emitting sources 12.

In an embodiment, each of the plurality of light emitting sources 12 can have a pixel characteristic radius that ranges from approximately 1/10 millimeter to approximately 1 centimeter. In an embodiment, a total area coverage of the plurality of light emitting sources 12 is at least 25% of the total area of the disinfecting pad 10. In an embodiment, the distance between each of the light emitting sources 12 is on the same order as the size of the light emitting source 12.

Each of the plurality of pixelated light emitting sources 12 can emit at least ultraviolet radiation. In an embodiment, the plurality of pixelated light emitting sources 12 can include any combination of one or more ultraviolet radiation emitters. Examples of ultraviolet radiation emitters can include, but are not limited to, high intensity ultraviolet lamps (e.g., high intensity mercury lamps), discharge lamps, UV LEDs, super luminescent LEDs, laser diodes, and/or the like. In one embodiment, the plurality of pixelated light emitting sources 12 can include a set of LEDs manufactured with one or more layers of materials selected from the group-III nitride material system (e.g., $Al_xIn_yGa_{1-x-y}N$, where $0 \le x$, $y \le 1$, and $x+y \le 1$ and/or alloys thereof). Additionally, the plurality of pixelated light emitting sources 12 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a waveguide, a plurality of ultraviolet fibers, each of which terminates at an opening, a diffuser, and/or the like.

The plurality of pixelated light emitting sources 12 can also comprise a complex optical device. For example, one or more of the plurality of pixelated light emitting sources 12 can include ultraviolet transparent lenses, ultraviolet reflective elements, such as reflective mirrors, ultraviolet diffusive elements, such as diffusively reflective surfaces, and/or the like. The optical properties of the pixelated light emitting sources 12 can change depending on the target requirements of radiation for each pixel. For example, each light emitting source 12 can include movable optical elements, such as lenses, mirrors, movable light scattering surfaces, and/or the like. In an embodiment, the light emitting source 12 can comprise an ultraviolet radiation source that is connected to a light guiding structure, such as an optical fiber, so that the light is directed from the optical fiber towards an object 14. It is understood that various light guiding and light scattering elements can be used to deliver the radiation to the object 14.

In an embodiment, the plurality of pixelated light emitting sources 12 can emit ultraviolet radiation for sterilization. For example, the ultraviolet wavelength range can be approximately 250 nanometers to approximately 300 nanometers. In one embodiment, the ultraviolet wavelength range can be approximately 270 nanometers to approximately 280 nanometers. The plurality of pixelated light emitting sources 12 can also emit ultraviolet radiation for the preservation (e.g., of produce, and/or the like) in the ultraviolet wavelength range of approximately 285 nanometers to approximately 300 nanometers. In an embodiment, for preservation, the peak wavelength is approximately 295 nanometers. In an embodiment, the intensity of the ultraviolet radiation of the plurality of pixelated light emitting sources 12 can be non-uniform and depend on the lateral location on the disinfecting pad 10 that is covered by the object 14. In a more specific embodiment, the intensity of the ultraviolet radiation of the plurality of pixelated light emitting sources 12 is higher in a central location of the object 14 than the intensity of the ultraviolet radiation of the plurality of pixelated light emitting sources 12 at the boundaries of the object 14.

Figure 3A:
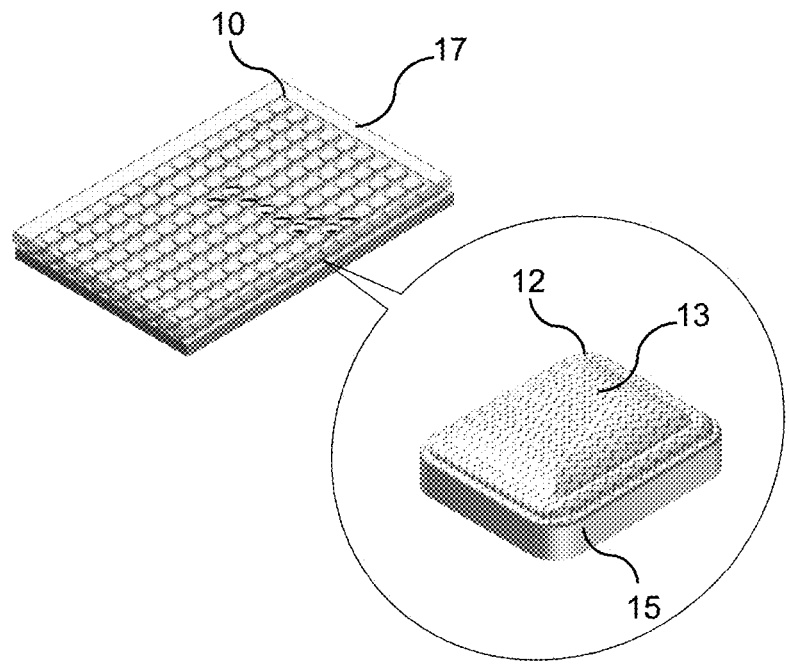
FIGS. 3A and 3B show a perspective view and a schematic of an illustrative light emitting source according to embodiments.

Each of the plurality of pixelated light emitting sources 12A that are located under the object 14A can sense that the object 14A is there before activation. In an embodiment, the disinfecting pad 10 can include a set of sensors that are located either within the pad or within each of the plurality of pixelated light emitting sources 12. For example, turning to FIGS. 3A and 3B, a perspective view of a light emitting source 12 and a schematic of a light emitting source 12 according to embodiments are, respectively, shown. In FIG. 3A, the light emitting source 12 an ultraviolet transparent encapsulating layer 13 and a package unit 15. The ultraviolet encapsulating layer 13 can comprise a window unit formed of silicon dioxide ($SiO_2$), aluminum oxide ($Al_2O_3$), calcium fluoride ($CaF_2$), magnesium fluoride ($MgF_2$), and/or the like, which allows ultraviolet light to be emitted from the light emitting source 12, without allowing environmental factors, such as humidity, affect the operation of the light emitting source 12. In an embodiment, the window unit 13 can incorporate optical elements such as lenses for controlling and directing the emitted light. In an alternative embodiment, the encapsulating layer 13 can comprise a fluoropolymer that is transparent to the ultraviolet radiation, such as fluorinated ethylene propylene co-polymer (EFEP), or Cytop®. The package unit 15 can include a printed board for operating light emitting source 12 and a protective enclosure that can be configured to reflect and direct ultraviolet light from the light emitting source 12. The package unit 15 can have anode and cathode electrodes that can be connected to the power supply unit. In an embodiment, the disinfecting pad 10 can include a transparent layer 17 that can overlay the plurality of light emitting sources 12 as a top pad layer. The transparent layer 17 is located between the light emitting source 12 and the object 14. In a more specific embodiment, the transparent layer can be a photocatalytic material, such as titanium oxide ($Ti_2O_3$).

In an embodiment, each light emitting source 12 can include a plurality of elements in order to detect the presence of an object. For example, in FIG. 3B, the light emitting source 12 includes an ultraviolet radiation source 16, a fluorescent source 18, a fluorescent sensor 20, a load/weight sensor 22, and an element 24 that can detect the presence of an object located over the light emitting source 12 (e.g., optoelectronic detector that detects reflected light to infer the presence of the object 14). It is understood that the light emitting source 12 can include other features not included in this figure. Furthermore, it is understood that these elements can be arranged in any order on the light emitting source 12 or the disinfecting pad 10.

In an embodiment, the fluorescent source 18 can emit radiation at a wavelength in order to elicit a fluorescent response from the object 14 (FIG. 1) located over the disinfecting pad 10. In an embodiment, the fluorescent source 18 emits UV-B, UV-A, or a deep blue light. The fluorescent sensor 20 can detect radiation to determine whether an object 14 (FIG. 1) is located over the disinfecting pad 10 or determine a location and/or concentration of microorganisms on the object 14. In an embodiment, the fluorescent signal that is detected by the fluorescent sensor 20 can determine the dose of ultraviolet radiation. In another embodiment, the load/weight sensor 22 can be configured to measure small deviations in weight to indicate that an object 14 is located over the disinfecting pad 10. For example, the load/weight sensor 22 can include small pillars that deform when the object 14 is placed over the light emitting source 12, which would indicate that the ultraviolet radiation source 16 can be activated. In another embodiment, the load/weight sensor 22 can include piezo-electric actuators. In determining the presence and location of the object 14, the set of sensors 20, 22, 24 can determine the boundaries of the object 14. In an embodiment, the boundary resolution of the object is at least 0.5 cm, where the boundary resolution is the partition of the objects boundary curve by discrete mesh points.

Figure 4:
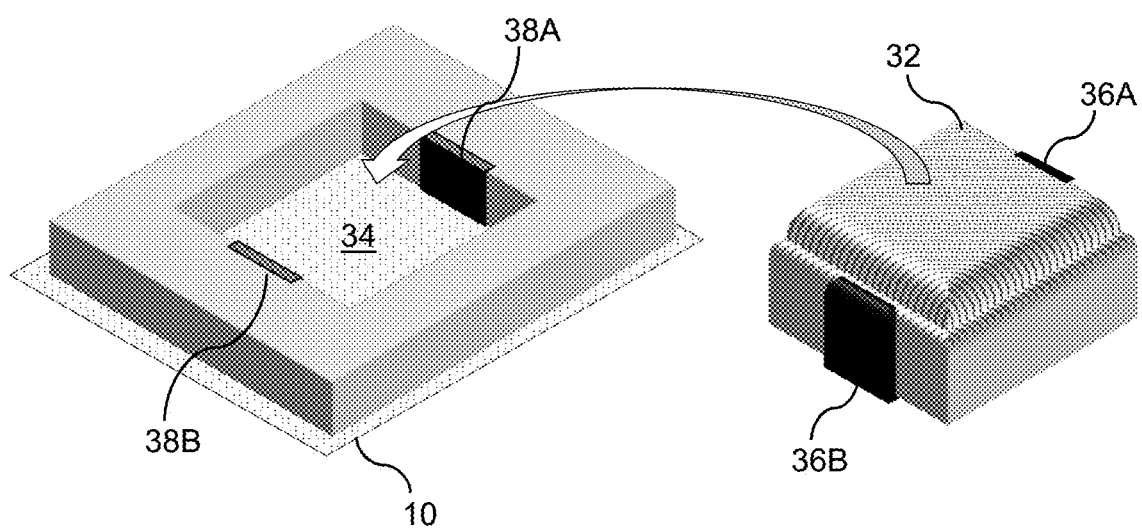
FIG. 4 shows an exploded view of an illustrative light emitting source according to an embodiment.

The plurality of pixelated light emitting sources can be attached to the disinfecting pad using any solution. Turning now to FIG. 4, a perspective view of a pixelated light emitting source 32 according to an embodiment is shown. Each of the pixelated light emitting sources 32 can be placed inside of a socket 34 that is attached to the disinfection pad 10. The pixelated light emitting source 32 includes a set of contacts 36A, 36B that connect to a corresponding set of contacts 38A, 38B within the socket 34. The connection between the set of contacts 36A, 36B, 38A, 38B can be facilitated using magnetic domains. The connection between the pixelated light emitting source 32 and the socket 34 should be sufficiently tight that the pixelated light emitting source 32 does not fall out of the socket 34 even if the disinfecting pad 10 is lifted up and turned upside down. However, the pixelated light emitting source 32 can be removed and replaced if it is ever defective.

Figure 5:
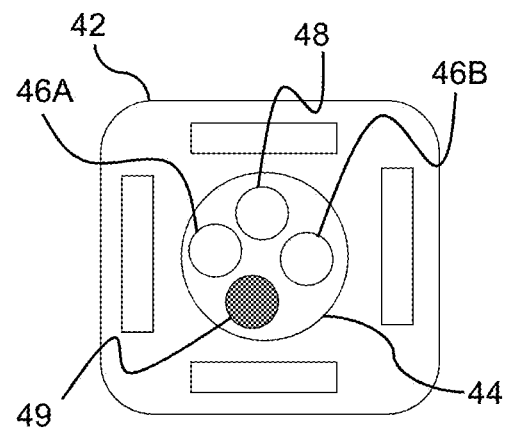
FIG. 5 shows a schematic of an illustrative light emitting source according to an embodiment.

Each of the pixelated light emitting sources can include other light sources, in addition to the ultraviolet radiation source. Turning now to FIG. 5, an illustrative light emitting source 42 according to an embodiment is shown. The light emitting source 42 can include features similar to the light emitting source 12 shown in FIG. 3B. However, the light emitting source 42 can also include an illuminating unit 44 that includes a set of ultraviolet radiation sources 46A, 46B, a visible light source 48, and a fluorescent source 49. In an embodiment, the illuminating unit 44 can include both a fluorescent unit 49 that operates as a source and a sensor. Although only two ultraviolet radiation sources 46A, 46B are shown and only one visible light source 48 is shown, it is understood that the illuminating unit 44 can include any number of ultraviolet radiation sources and any number of visible light sources. Also, it is understood that the set of ultraviolet radiation sources 46A, 46B, the visible light source 48, and the fluorescent source 49 can be in any configuration.

In an embodiment, the first ultraviolet radiation source 46A can operate at a first target peak wavelength with the Full Width at Half Maximum (FWHM) being 5 to 50 nanometers, while the second ultraviolet radiation source B can operate at a second target peak wavelength with the FWHM being 5 to 50 nanometers. In a more specific embodiment, the first ultraviolet radiation source 46A can operate at a peak wavelength of 275 nanometers, while the second ultraviolet radiation source 46B can operate at a peak wavelength of 295 nanometers. In an embodiment, the set of visible light sources 48A, 48B can operate at 450 nanometers and 650 nanometers. It is understood that the peak wavelength of the ultraviolet radiation sources 46A, 48B and the set of visible light sources 48A, 48B can be different based on the application. In an embodiment, at least one of the ultraviolet radiation sources 46A, 46B operates at either 275 nanometers or 295 nanometers, with a tolerance of +/−10 nanometers.

Figure 6:
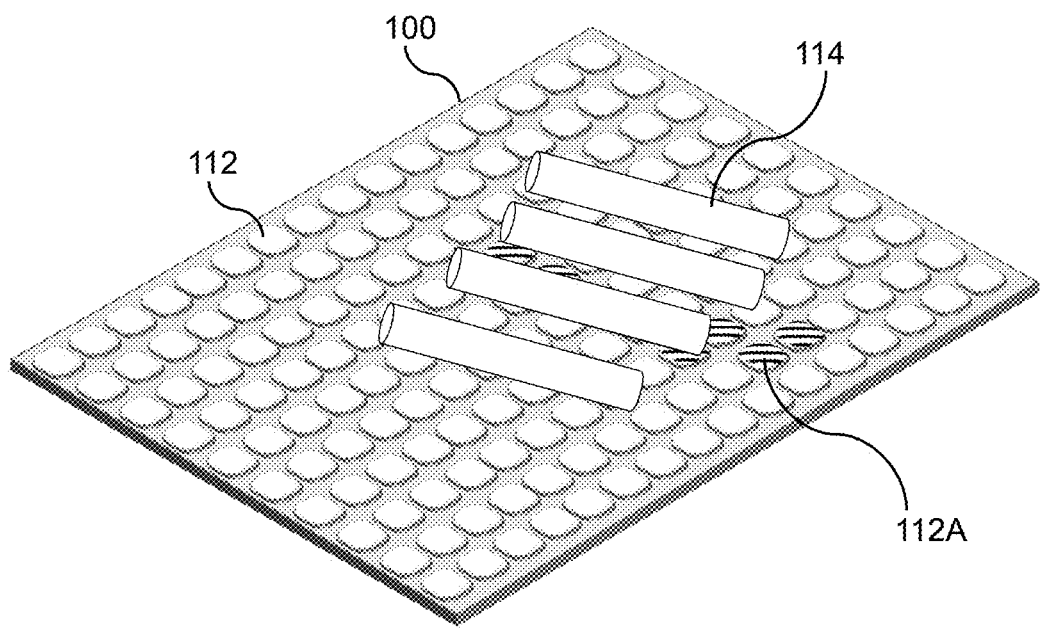
FIG. 6 shows a perspective view of an illustrative disinfecting pad according to an embodiment.

It is understood that the disinfecting pad according to any of the embodiments discussed herein can be used to disinfect anything, including surfaces/objects, plants, and/or the like, preserve the lifetime of food items, or treat skin related ailments. In an embodiment, the disinfecting pad can be used to disinfect a liquid. Turning now to FIG. 6, a perspective view of an illustrative disinfecting pad 100 according to an embodiment is shown. The disinfecting pad 100 can include any of the features discussed in the embodiments shown in FIGS. 1-5. A set of enclosures 114 can be located on top of the disinfecting pad 100 in order to disinfect a liquid within the enclosure 114. The set of enclosures 114 can be formed on an ultraviolet transparent material, such as $SiO_2$, a fluoropolymer, and/or the like. In an embodiment, the liquid within the set of enclosures 114 can enclose a liquid that requires disinfection, such as blood.

Figure 7:
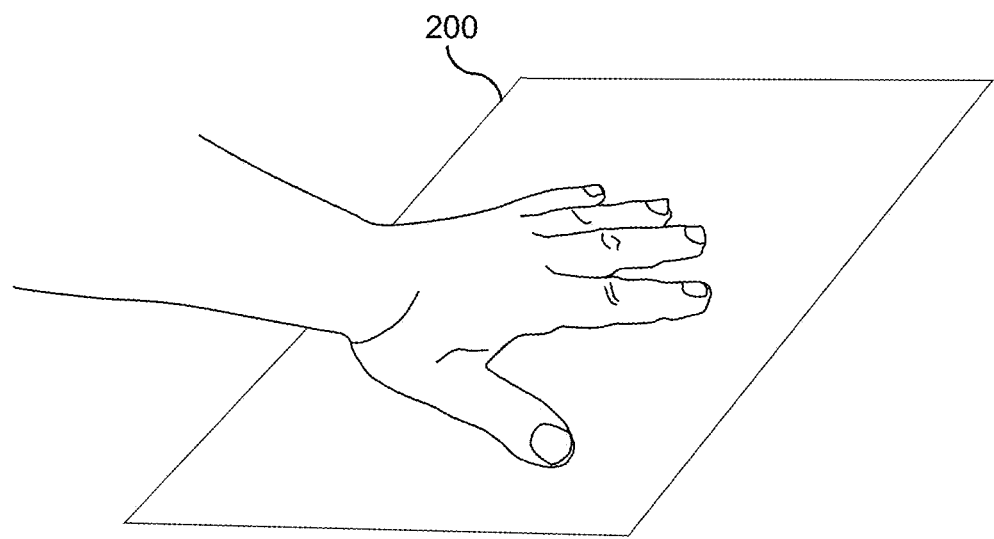
FIG. 7 shows a perspective view of an illustrative disinfecting pad according to an embodiment.

In an embodiment, a disinfecting pad can be used to disinfect a body part, such as a hand. Turning now to FIG. 7, a perspective view of an illustrative disinfecting pad 200 according to an embodiment is shown. The disinfecting pad 200 can include any of the features discussed in the embodiments shown in FIGS. 1-5. The set of pixelated light emitting sources are omitted from this figure for clarity purposes only and it is understood that the disinfecting pad 200 includes them. As seen in the figure, a hand 214 is placed over the disinfecting pad 200 in order to disinfect the underside of the hand 214.

In any of the embodiments of the disinfecting pad discussed in FIGS. 1-7, an ultraviolet absorbing cover can be placed over the pad in order to prevent the ultraviolet radiation from entering the ambient. However, it is understood that since only the sources that are located underneath the object are activated, ultraviolet radiation should not enter the ambient.

Figure 8:
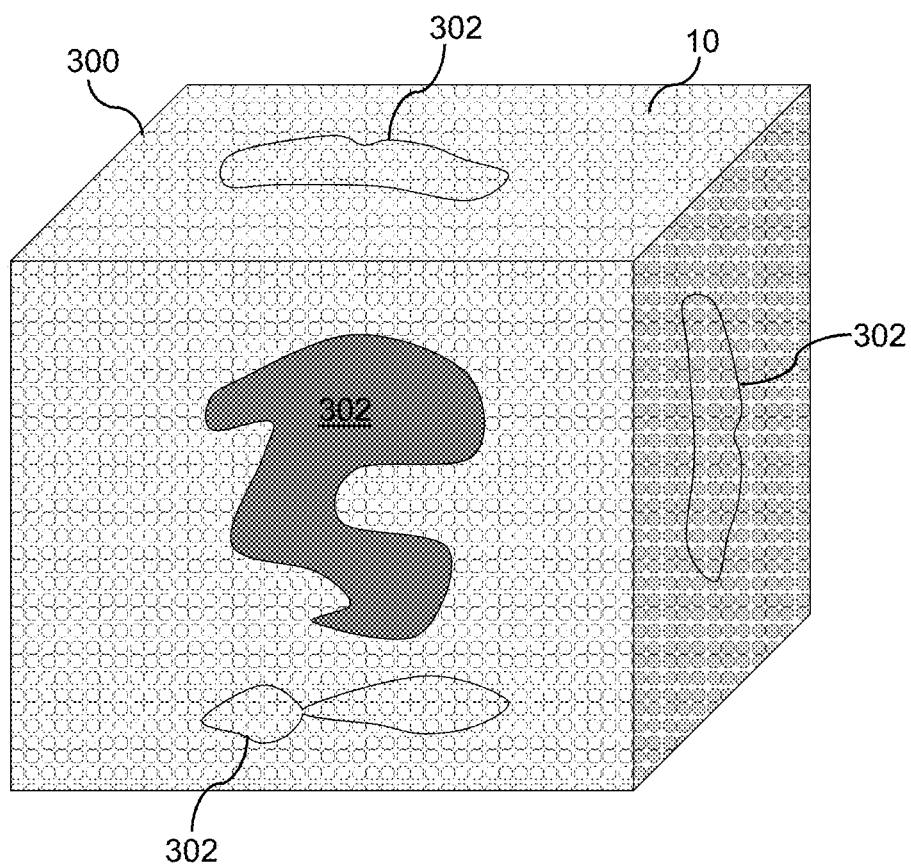
FIG. 8 shows a perspective view of an illustrative disinfecting pad according to an embodiment.

Turning now to FIG. 8, a perspective view of an illustrative enclosure 300 according to an embodiment is shown. The enclosure 300 is shown as a 3-dimensional shape, e.g., a cube, wherein an interior of at least one side of the enclosure 300 includes a disinfecting pad 10 according to any of the embodiments discussed in FIGS. 1-5. Therefore, an object placed within the enclosure 300 can be radiated from all sides. In an embodiment, all of the ultraviolet radiation sources on all of the disinfecting pads 10 can be activated. In another embodiment, only the ultraviolet radiation sources that are covered by the projections 302 from the object within the enclosure 300 are activated.

Figure 9:
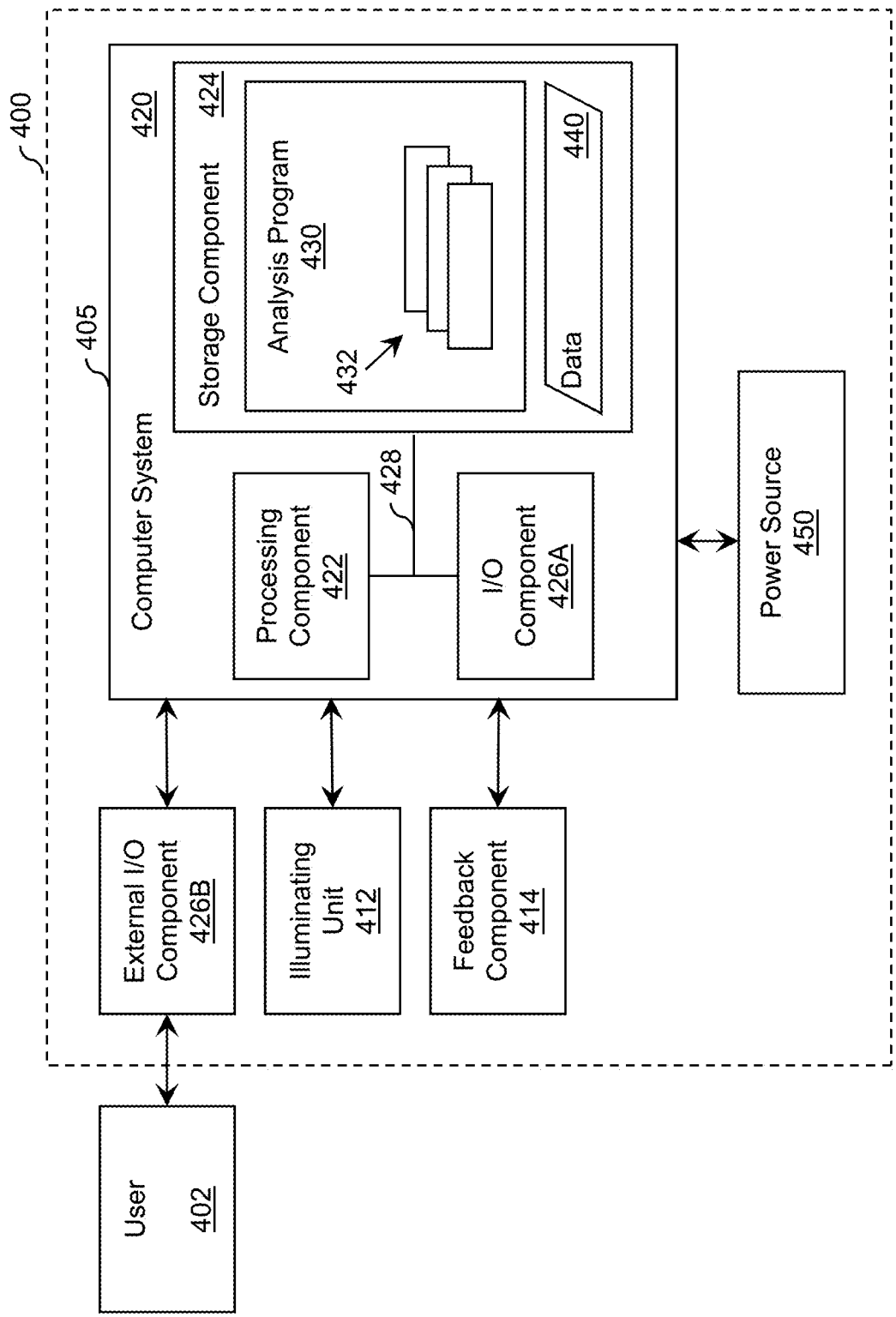
FIG. 9 shows a schematic of an illustrative system for use with a disinfecting pad according to an embodiment.
Figure 10:
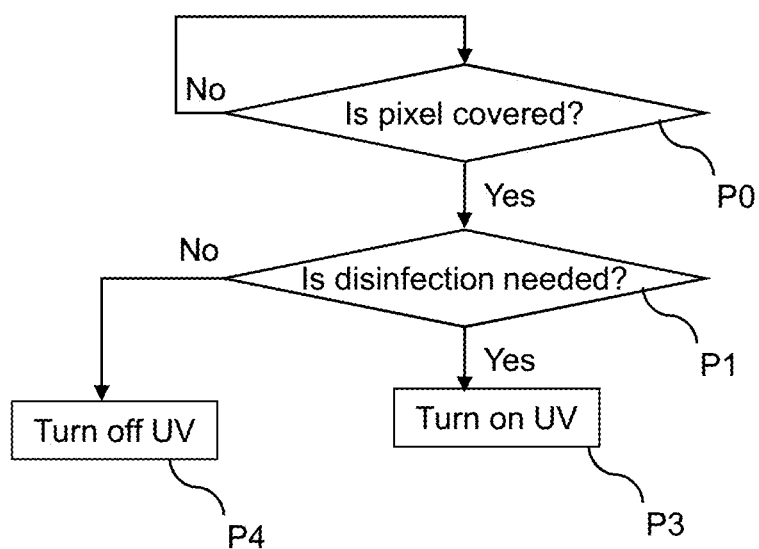
FIG. 10 shows a flow diagram of an illustrative method of operating the system for a disinfecting pad according to an embodiment.

FIG. 9 shows a schematic of an illustrative system 400 that can be implemented with any of the embodiments depicted in FIGS. 1-8 and perform the flow diagram depicted in FIG. 10 according to an embodiment. In this embodiment, the system 400 is shown including the illuminating unit 412 that includes the set of ultraviolet radiation sources 46A, 46B and set of visible light sources 48A, 48B (FIG. 5) and a feedback component 414 that includes the set of sensors 20, 22 24 (FIG. 3B).

As depicted in FIG. 9, the system 400 can include a control unit 405. It is understood that the control unit 405 can be located within the disinfecting pad in any of the embodiments discussed in FIGS. 1-8. In one embodiment, the control unit 405 can be implemented as a computer system 420 including an analysis program 430, which makes the computer system 420 operable to manage the illuminating unit 412 and the feedback component 414 in the manner described herein. In particular, the analysis program 430 can enable the computer system 420 to operate the ultraviolet radiation sources and/or the visible lights sources in the illuminating unit 412 in order to generate and direct ultraviolet radiation and/or visible radiation towards an object located on a disinfecting pad. The computer system 420 can also process data corresponding to one or more attributes regarding the object, which can be acquired by the feedback component 414, and/or an ultraviolet radiation history stored as data 440. The computer system 420 can individually control each ultraviolet radiation source and visible light source in the illuminating unit 412 and sensor in the feedback component 414 and/or control two or more of the ultraviolet radiation sources, the visible light sources, and the sensors as a group. Furthermore, the ultraviolet radiation sources in the illuminating unit 412 can emit ultraviolet radiation of substantially the same wavelength or of multiple distinct wavelengths.

In an embodiment, during an initial period of operation, the computer system 420 can acquire data from at least one of the sensors in the feedback component 414 regarding one or more attributes of the object and generate data 440 for further processing. The data 440 can include information regarding a presence of an object, a weight of an object, a microorganism concentration and/or location on the object, a size of an object, and/or the like. The computer system 420 can use the data 440 to control one or more aspects of the ultraviolet radiation generated by the ultraviolet radiation source(s) of the illuminating unit 412 during an illumination period.

Furthermore, one or more aspects of the operation of the ultraviolet radiation sources of the illuminating unit 412 can be controlled or adjusted by a user 402 via an external interface I/O component 426B. The external interface I/O component 426B can be located on the exterior of the system 400, and used to allow the user 402 to selectively turn on/off the ultraviolet radiation sources in the illuminating unit 412.

The external interface I/O component 426B can include, for example, a touch screen that can selectively display user interface controls, such as control dials, which can enable the user 402 to adjust one or more of: an intensity, scheduling, and/or other operational properties of the set of ultraviolet radiation sources in the illuminating unit 412 (e.g., operating parameters, radiation characteristics). In an embodiment, the external interface I/O component 426B could conceivably include a keyboard, a plurality of buttons, a joystick-like control mechanism, and/or the like, which can enable the user 402 to control one or more aspects of the operation of the set of ultraviolet radiation sources in the illuminating unit 412. The external interface I/O component 426B also can include any combination of various output devices (e.g., an LED, a visual display), which can be operated by the computer system 420 to provide status information pertaining to the illumination period of the object for use by the user 402. For example, the external interface I/O component 426B can include one or more LEDs for emitting a visual light for the user 402, e.g., to indicate a status of the illumination period. In an embodiment, the external interface I/O component 426B can include a speaker for providing an alarm (e.g., an auditory signal), e.g., for signaling that ultraviolet radiation is being generated or that the object had been illuminated by ultraviolet radiation.

The computer system 420 is shown including a processing component 422 (e.g., one or more processors), a storage component 424 (e.g., a storage hierarchy), an input/output (I/O) component 426A (e.g., one or more I/O interfaces and/or devices), and a communications pathway 428. In general, the processing component 422 executes program code, such as the analysis program 430, which is at least partially fixed in the storage component 424. While executing program code, the processing component 422 can process data, which can result in reading and/or writing transformed data from/to the storage component 424 and/or the I/O component 426A for further processing. The pathway 428 provides a communications link between each of the components in the computer system 420. The I/O component 426A and/or the external interface I/O component 426B can comprise one or more human I/O devices, which enable a human user 402 to interact with the computer system 420 and/or one or more communications devices to enable a system user 402 to communicate with the computer system 420 using any type of communications link. To this extent, during execution by the computer system 420, the analysis program 430 can manage a set of interfaces (e.g., graphical user interface(s), application program interface, and/or the like) that enable human and/or system users 402 to interact with the analysis program 430. Furthermore, the analysis program 430 can manage (e.g., store, retrieve, create, manipulate, organize, present, etc.) the data, such as data 440, using any solution.

In any event, the computer system 420 can comprise one or more general purpose computing articles of manufacture (e.g., computing devices) capable of executing program code, such as the analysis program 430, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 430 can be embodied as any combination of system software and/or application software.

Furthermore, the analysis program 430 can be implemented using a set of modules 432. In this case, a module 432 can enable the computer system 420 to perform a set of tasks used by the analysis program 430, and can be separately developed and/or implemented apart from other portions of the analysis program 430. When the computer system 420 comprises multiple computing devices, each computing device can have only a portion of the analysis program 430 fixed thereon (e.g., one or more modules 432). However, it is understood that the computer system 420 and the analysis program 430 are only representative of various possible equivalent monitoring and/or control systems that may perform a process described herein with regard to the control unit, the ultraviolet radiation sources and the sensors. To this extent, in other embodiments, the functionality provided by the computer system 420 and the analysis program 430 can be at least partially implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of the disinfecting pad. Illustrative aspects of the invention are further described in conjunction with the computer system 420. However, it is understood that the functionality described in conjunction therewith can be implemented by any type of monitoring and/or control system.

Regardless, when the computer system 420 includes multiple computing devices, the computing devices can communicate over any type of communications link. Furthermore, while performing a process described herein, the computer system 420 can communicate with one or more other computer systems, such as the user 402, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 9 can receive power from a power source 450. The power source 450 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power source can include solar, a mechanical energy to electrical energy converter such as a rechargeable device, etc.

Figure 3B:
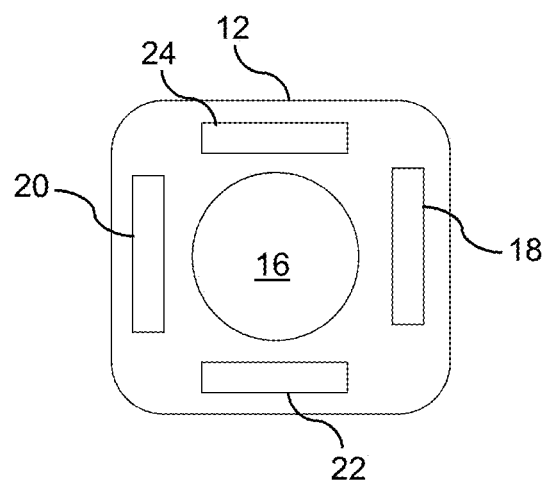

FIG. 10 shows a flow diagram of an illustrative method of operating the system 400 shown in FIG. 9 according to an embodiment, which can be implemented by the computer system 420. The computer system 420 can be configured to control the set of ultraviolet radiation sources in the illuminating unit 412 to direct ultraviolet radiation at an object located on a disinfecting pad. The feedback component 414 is configured to acquire data regarding the object located over the disinfecting pad. As illustrated in FIG. 3B, the feedback component 414 can include a plurality of sensors 20, 22, 24, each of which can acquire data used by the computer system 420 to monitor the object(s).

At P0, the computer system 420, e.g., via a sensor in the feedback component 414, can determine whether the pixelated light emitting source 12 (FIG. 1) is covered by an object. If the pixel is not covered, then the computer system 420 can continue at P0 and determine whether the pixelated light emitting source 12 is covered. If the pixel is covered, then the computer system 420, via a sensor in the feedback component 414, can determine whether the object requires disinfection. If the object does require disinfection, at P3, the computer system 420 can turn on the set of ultraviolet radiations in the illuminating array 412. If the object does not require disinfection, at P4, the computer system 420 can keep the set of ultraviolet radiations turned off.

Figure 11:
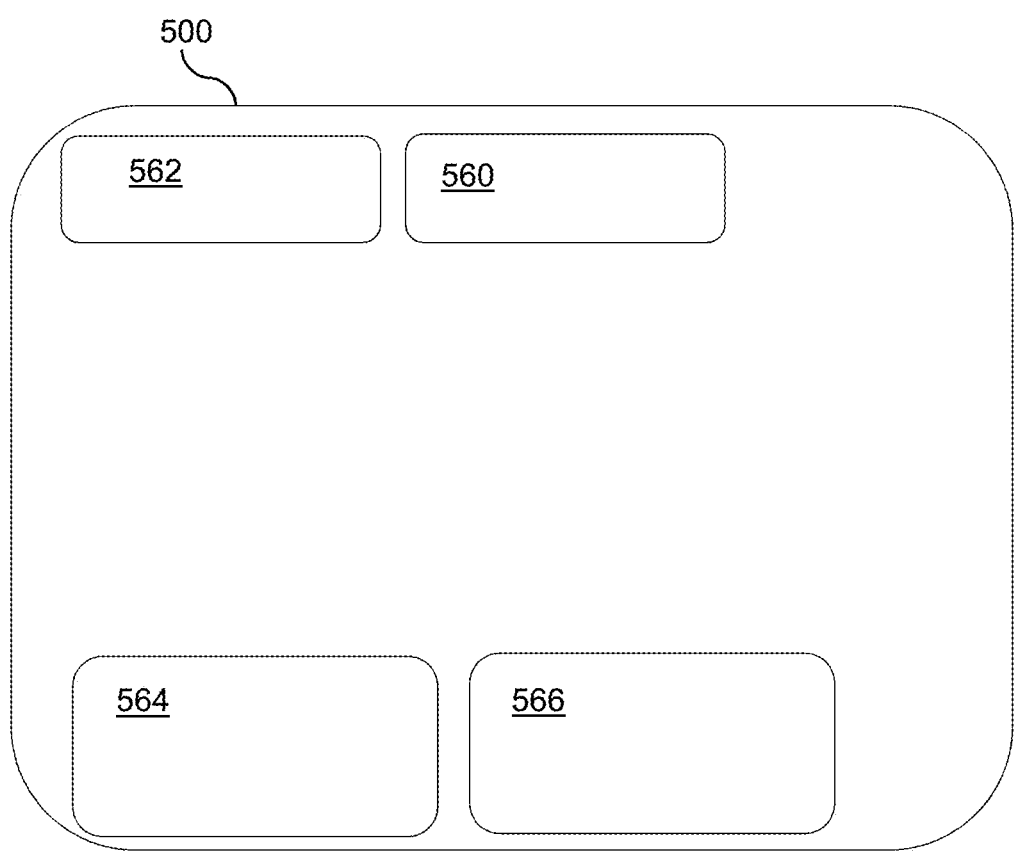
FIG. 11 shows a schematic of an illustrative disinfecting pad according to an embodiment.

Turning now to FIG. 11, a schematic of an illustrative disinfecting pad 500 according to an embodiment. The disinfecting pad 500 can include any of the features discussed in the embodiments shown in FIGS. 1-8. In addition, the disinfecting pad 500 can include a message area 560 that can inform a user the status of the disinfection and/or the radiation of the object, such as, the radiation dose, the radiation time, the time remaining for radiation, and/or the like. The disinfecting pad 500 can also include a WiFi transmitter 562 that can be controlled by a user using a remote interface (e.g., a smart phone or device). The disinfecting pad 500 can also include a storage unit (e.g., the storage component 424 (FIG. 9)), which can be a solid-state storage card 564, as shown in FIG. 11. The disinfecting pad 500 can also include an auxiliary unit 566 that can be a visible indicator that the disinfecting pad 500 is working. In addition, the disinfecting pad 500 can be wireless (through WiFi or Bluetooth) and/or connected via wires to external devices such as cameras, microphones, computers etc. The pad can be activated by placing the object on the pad, and can comprise a notification system such as visible indicator that the pad is working.

Figure 12:
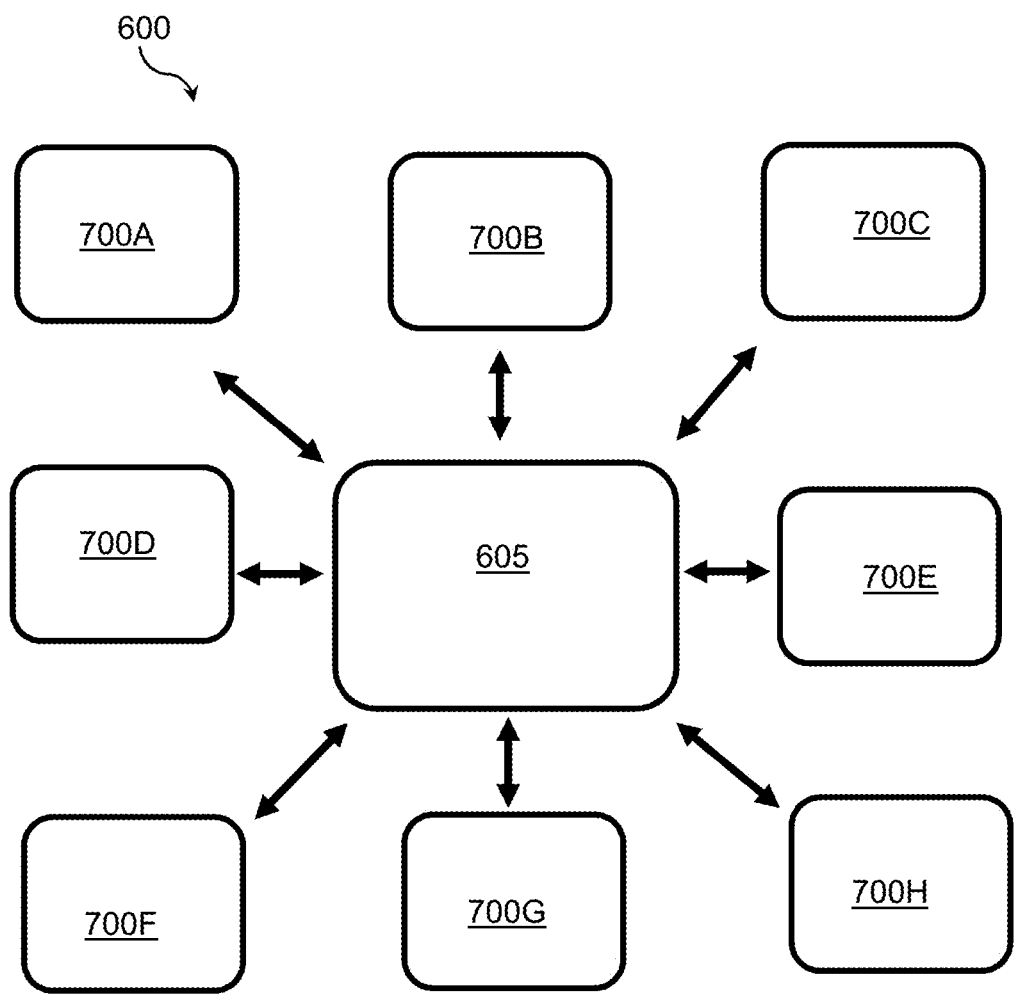
FIG. 12 shows a schematic of an illustrative system including a plurality of disinfecting pads according to an embodiment.

Turning now to FIG. 12, a schematic of an illustrative system 600 according to an embodiment is shown. This system 600 shows that a plurality of disinfecting pads 700A-H can be connected via WiFi, Bluetooth, wires, and/or the like, to a single control unit 605 for communication and control of the plurality of disinfecting pads 700A-H.

In an embodiment, a first disinfecting pad 700A can be designed to contaminate an object 14 (FIG. 1) with a predefined contaminant that is easily identifiable through fluorescent. A second disinfecting pad 700B can include a cleaning system that includes mechanical mechanisms for physically cleaning the object. For example, the cleaning system can include a liquid (e.g., water) for cleaning the object, brushes, and/or the like that is known in the art. The second disinfecting pad 700B can include a visual signal that informs a user that the cleaning has been completed. A third disinfecting pad 700C can include a plurality of pixelated light emitting sources 12 according to any of the embodiments discussed herein.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system, comprising:
   a flexible pad for disinfecting at least one object;
   a plurality of pixelated light emitting sources located on the flexible pad in an array, wherein a pixel characteristic radius is approximately 1/10 millimeter to approximately 1 centimeter and the plurality of pixelated light emitting sources covers at least 25% of the flexible pad, and wherein each of the plurality of pixelated light emitting sources includes at least one ultraviolet radiation source and at least one fluorescent source, wherein the at least one fluorescent source is configured to elicit a fluorescent signal from the object;

a set of sensors for acquiring data for the at least one object, wherein the set of sensors includes a fluorescent sensor, and wherein the data includes a presence and a location of the at least one object and the fluorescent signal, wherein the fluorescent signal indicates a location and a concentration of microorganisms; and a control system for monitoring and controlling the plurality of pixelated light emitting sources and the set of sensors, the monitoring and controlling including:

selectively operating the at least one ultraviolet radiation source of each of the plurality of pixelated light emitting sources based on the presence and the location of the at least one object and the location and the concentration of microorganisms.

2. The system of claim 1, wherein the at least one ultraviolet radiation source operates in the range of 250 nanometers to 300 nanometers.

3. The system of claim 2, wherein the at least one ultraviolet radiation source operates in the range of 290 nanometers to 300 nanometers.

4. The system of claim 1, wherein the control system only turns on a set of pixelated light emitting sources in the plurality of light emitting sources that are located underneath the object.

5. The system of claim 1, wherein each of the plurality of pixelated light emitting sources includes at least one visible source operating in the range of 450 nanometers to 650 nanometers.

6. The system of claim 1, wherein each of the plurality of pixelated light emitting sources includes the set of sensors.

7. The system of claim 1, wherein the set of sensors includes a load sensor configured to determine a deviation in weight due to the object.

8. The system of claim 1, wherein the set of sensors includes at least one optoelectronic detector configured to detect reflected light in order to infer the presence of the at least one object.

9. The system of claim 1, wherein an intensity of the operating ultraviolet radiation sources is non-uniform.

10. A system, comprising:
a flexible pad for disinfecting at least one object;
a plurality of pixelated light emitting sources located on the flexible pad in an array, wherein a pixel characteristic radius is approximately ¹⁄₁₀ millimeter to approximately 1 centimeter and the plurality of pixelated light emitting sources covers at least 25% of the flexible pad, and wherein each of the plurality of pixelated light emitting sources includes:
at least one ultraviolet radiation source configured to generate ultraviolet radiation; and
a set of sensors for acquiring data for the at least one object, wherein the set of sensors includes at least one optoelectronic detector, and wherein the data includes a presence and a location of the at least one object; and
a control system for monitoring and controlling the plurality of pixelated light emitting sources and the set of sensors, the monitoring and controlling including:
operating the at least one optoelectronic detector to detect light in order to infer the presence of the at least one object; and
selectively operating the at least one ultraviolet radiation source of each of the plurality of pixelated light emitting sources based on the presence and the location of the at least one object.

11. The system of claim 10, wherein the at least one ultraviolet radiation source operates in the range of 250 nanometers to 300 nanometers.

12. The system of claim 11, wherein the at least one ultraviolet radiation source operates in the range of 290 nanometers to 300 nanometers.

13. The system of claim 10, wherein the control system only turns on a set of pixelated light emitting sources in the plurality of light emitting sources that are located underneath the object.

14. The system of claim 10, wherein each of the plurality of pixelated light emitting sources includes at least one visible source operating in the range of 450 nanometers to 650 nanometers.

15. The system of claim 10, wherein the set of sensors includes a load sensor configured to determine a deviation in weight due to the object.

16. The system of claim 10, wherein the set of sensors includes a fluorescent sensor configured to determine a fluorescent signal that indicates a location and a concentration of microorganisms.

17. The system of claim 10, wherein an intensity of the operating ultraviolet radiation sources is non-uniform.

18. A system, comprising:
a flexible pad for disinfecting at least one object;
a plurality of pixelated light emitting sources located on the flexible pad in an array, wherein a pixel characteristic radius is approximately ¹⁄₁₀ millimeter to approximately 1 centimeter and the plurality of pixelated light emitting sources covers at least 25% of the flexible pad, and wherein each of the plurality of pixelated light emitting sources includes:
at least one ultraviolet radiation source configured to generate ultraviolet radiation;
a set of visible light sources configured to operate in the range of 450 nanometers to 650 nanometers; and
a set of sensors for acquiring data for the at least one object, wherein the set of sensors includes at least one optoelectronic detector, and wherein the data includes a presence and a location of the at least one object; and
a control system for monitoring and controlling the plurality of pixelated light emitting sources and the set of sensors, the monitoring and controlling including:
operating the set of visible light sources and at least one optoelectronic detector to detect light in order to infer the presence of the at least one object; and
selectively operating the at least one ultraviolet radiation source of each of the plurality of pixelated light emitting sources based on the presence and the location of the at least one object.

19. The system of claim 18, wherein the control system only turns on a set of pixelated light emitting sources in the plurality of light emitting sources that are located underneath the object.

20. The system of claim 18, wherein the set of sensors includes at least one of: a load sensor configured to determine a deviation in weight due to the at least one object or a fluorescent sensor configured to determine a fluorescent signal that indicates a location and a concentration of microorganisms.

* * * * *